(12) United States Patent
Lebedev et al.

(10) Patent No.: US 9,857,278 B2
(45) Date of Patent: Jan. 2, 2018

(54) APPARATUS FOR AND A METHOD OF CHARACTERISING MECHANICAL PROPERTIES OF A SAMPLE

(75) Inventors: Maxim Lebedev, Bateman (AU); Vassily Mikhaltsevitch, Rivervale (AU); Mark Lwin, Rivervale (AU); Boris Gurevich, Dianella (AU)

(73) Assignee: Curtin University of Technology, Bentley (AU)

( * ) Notice: Subject to any disclaimer, the term of this patent is extended or adjusted under 35 U.S.C. 154(b) by 312 days.

(21) Appl. No.: 13/880,364

(22) PCT Filed: Oct. 18, 2011

(86) PCT No.: PCT/AU2011/001324
§ 371 (c)(1),
(2), (4) Date: Apr. 18, 2013

(87) PCT Pub. No.: WO2012/051647
PCT Pub. Date: Apr. 29, 2012

(65) Prior Publication Data
US 2013/0213120 A1    Aug. 22, 2013

(30) Foreign Application Priority Data

Oct. 18, 2010    (AU) .............................. 2010904640

(51) Int. Cl.
*G01N 3/00*    (2006.01)
*G01N 3/32*    (2006.01)
*G01N 33/38*    (2006.01)

(52) U.S. Cl.
CPC ................. *G01N 3/00* (2013.01); *G01N 3/32* (2013.01); *G01N 33/38* (2013.01); *G01N 2203/0019* (2013.01); *G01N 2203/0242* (2013.01)

(58) Field of Classification Search
CPC ............... G01N 2203/0254; G01N 2203/0256
See application file for complete search history.

(56) References Cited

U.S. PATENT DOCUMENTS

| 4,379,407 A * | 4/1983 | Masse | ...................... G01N 3/32 73/579 |
| 5,025,668 A * | 6/1991 | Sarda et al. | ...................... 73/795 |

(Continued)

FOREIGN PATENT DOCUMENTS

| SU | 1051409 A | 10/1983 |
| SU | 1236344 A1 | 6/1986 |

(Continued)

OTHER PUBLICATIONS

International Search Report dated Nov. 21, 2011 in PCT Application No. PCT/AU2011/001324 filed Oct. 18, 2011.

*Primary Examiner* — R. A. Smith
*Assistant Examiner* — Herbert K Roberts
(74) *Attorney, Agent, or Firm* — Kilpatrick Townsend & Stockton LLP

(57) ABSTRACT

The present disclosure provides an apparatus for characterizing mechanical properties of a sample. The apparatus comprises a structure for supporting the sample and applying a first pressure in a first direction to the sample and an actuator for modulating the first pressure. The apparatus also comprises a pressure applicator containing a liquid and arranged to apply a second pressure to the sample in a second direction that is transversal to the first direction. Further, the apparatus comprises a pore pressure applicator arranged to apply a flow of a fluid through a porous sample such that a pore pressure is applied to the porous sample. In addition, the apparatus comprises a sensor for sensing a change in the sample in response to a change in a pressure experienced by the sample.

1 Claim, 4 Drawing Sheets

(56) References Cited

U.S. PATENT DOCUMENTS

| | | | | | |
|---|---|---|---|---|---|
| 5,253,518 | A | * | 10/1993 | Steiger | E21B 49/006 166/250.01 |
| 5,959,215 | A | * | 9/1999 | Ono | G01N 3/36 73/789 |
| 6,591,690 | B1 | * | 7/2003 | Crockford | G01N 3/10 73/760 |
| 2004/0139804 | A1 | * | 7/2004 | Takada et al. | 73/760 |
| 2007/0144249 | A1 | * | 6/2007 | Masuda | E02D 1/00 73/152.59 |

FOREIGN PATENT DOCUMENTS

| | | | | |
|---|---|---|---|---|
| WO | WO 9837400 A1 | * | 8/1998 | G01N 3/32 |
| WO | WO9837400 A1 | | 8/1998 | |

\* cited by examiner

APPARATUS FOR AND A METHOD OF CHARACTERISING MECHANICAL PROPERTIES OF A SAMPLE

CROSS-REFERENCE TO RELATED APPLICATIONS

This application is a US National Phase under 35 USC 371 of PCT Application No. PCT/AU2011/001324 filed Oct. 18, 2011 which claims priority to Australian Application No. 2010904640 filed on Oct. 18, 2010, the disclosures of which are incorporated by reference herein.

FIELD OF THE INVENTION

The present invention relates to an apparatus for characterising mechanical properties of a sample. In particular, though not exclusively, the present invention relates to an apparatus for simulating conditions that the sample would experience in a subsurface location, and for characterizing elastic or anelastic properties of the sample.

BACKGROUND OF THE INVENTION

Information obtained in geological surveys using sonic and/or seismic waves (relatively low frequency waves) needs to be interpreted.

A common way of doing this is to take a sample, such as a core sample, from the region where the geological survey was taken and to subject the sample to typical subsurface conditions, such as stresses and pore fluid pressures. The sample is then analysed using ultrasonic waves (relatively high frequency waves) and obtained results are corrected such that at least some information for low frequency conditions can be estimated. However, such corrections introduce many uncertainties.

Consequently, it is desirable to acquire low frequency data of samples directly. So far, such attempts have been limited by technical constraints. In one known arrangement for measuring at low frequency, the entire measurement apparatus with sample is positioned in a pressure vessel to simulate subsurface conditions and low frequency measurements of the sample are taken within the pressure vessel. One disadvantage of this device is the limited range of pressures at which it can operate. A further disadvantage arises from the resonance frequency of the measurement apparatus. The measurement apparatus needs to be relatively small in order to be accommodated in a suitable pressure chamber. Such relatively small apparatus have relatively high resonance frequency (for example in the 10-20 Hz range), which limits the frequency range at which measurements can be taken. Further, the resonance frequency of the measurement apparatus is different within the pressure cell and outside the pressure cell and it is not a trivial task to identify contribution of such resonances for correction of data. An additional practical disadvantage is that the sample can only be relatively small.

In the light of the above, there exists a need for technological advancement.

SUMMARY OF THE INVENTION

In accordance with a first aspect of the present invention, there is provided an apparatus for characterising mechanical properties of a sample, the apparatus comprising:

a structure for supporting the sample and applying a first pressure in a first direction to the sample;

an actuator for modulating the first pressure;

a pressure applicator containing a liquid and arranged to apply a second pressure to the sample in a second direction that is transversal to the first direction;

a pore pressure applicator arranged to apply a flow of a fluid through a porous sample such that a pore pressure is applied to the porous sample; and a sensor for sensing a change in the sample in response to a change in a pressure experienced by the sample.

Having the pressure applicator arranged to apply a pressure to the sample in a second direction that is transversal to the first direction provides the significant advantage of allowing the first and second pressures to be controlled independently. In particular, such an arrangement allows the apparatus to simulate anisotropic stress conditions that would be experienced in typical subsurface locations.

The mechanical properties may be elastic or anelastic properties.

The second pressure may be applied in any direction that is transversal to a direction of the first pressure and typically is applied in multiple directions, such as a radial pressure.

The apparatus typically has a mass that is selected such that the resonance frequency of the apparatus is 0.1 Hz or less. Having a resonance frequency that is 0.1 Hz or less provides the significant advantage of allowing providing an extended frequency range of measurement, such as from 0 Hz to approximately 20 Hz.

The pressure applicator containing a liquid typically comprises a flexible member that is in contact with the sample and the liquid is in contact with the member such that the second pressure is transferred to the sample via the liquid and the member.

In one embodiment, at least some of the mass is provided by a mass plate arranged at substantially one end of the apparatus. In an alternative embodiment, two mass plates may be provided, wherein the sample is located between the two mass plates.

A ratio of a mean of the first pressure to the amount of modulation of the first pressure caused by the actuator may be in the order of $10^3$ to $10^6$.

The structure of the apparatus may be a mechanical structure that comprises at least one portion that contact the sample either directly or indirectly and apply the first pressure to the sample.

The sample typically is rock, hard earth, a core sample, or any other appropriate sample taken from a subsurface location.

The apparatus may comprise a hydraulic piston arrangement for applying the first pressure to the sample. In an alternative, the first pressure may be applied by opposing pistons, such as opposing hydraulic pistons. Each piston may be independently controllable.

In the above embodiments, the piston or pistons may be damped so as to further reduce the resonance frequency of the apparatus.

The actuator typically is a piezoelectric actuator. The actuator may be arranged so as to modulate the first pressure at a frequency from 0 Hz to 20 kHz. The actuator typically is positioned between the piston, or one of the pistons, and the sample. Alternatively, the piston, or one of the pistons, may be positioned between the actuator and the sample.

Resonant vibrations of the apparatus may be reduced by arranging the apparatus on a vibration damper.

In accordance with a second aspect of the present invention, there is provided a method of characterising mechanical properties of a sample, the method comprising the steps of:

providing the sample;
applying a first pressure in a first direction to the sample;
modulating the first pressure;
applying a second pressure to the sample in a second direction that is transversal to the first direction; the second pressure being applied via a liquid that transfers the second pressure either directly or indirectly to the sample;
sensing a change in the sample in response to a change in a pressure experienced by the sample; and
characterising the mechanical properties of the sample from the sensed change in the sample.

The step of applying a second pressure to the sample typically comprises applying the second pressure via a liquid that transfers the second pressure indirectly to the sample.

The step of characterising the mechanical properties typically also comprises determining Poisson's ratio as the ratio of the sensed changes; and determining Young's modulus of the sample by taking into account a bulk modulus of the liquid via which the second pressure is applied.

The first pressure typically is modulated periodically.

In one specific embodiment the method comprises the steps of:
detecting a first signal proportional to a strain and associated with the first pressure, the first signal being detected at a location between an actuator modulating the first pressure and the sample;
detecting a second signal proportional to a strain and associated with the second pressure, the second signal being detected at a location such that the sample is located between that location and an actuator for applying the second pressure. Further, the method typically comprises the steps of determining a phase shift between the first and the second signals; and using the phase shift between the first and the second signals to determine an extensional attenuation in the sample.

BRIEF DESCRIPTION OF THE DRAWINGS

In order that the present invention may be more clearly ascertained, embodiments of the present invention will now be described, by way of example only, with reference to the accompanying drawings, in which.

DETAILED DESCRIPTION OF THE EMBODIMENTS

Figure 1:
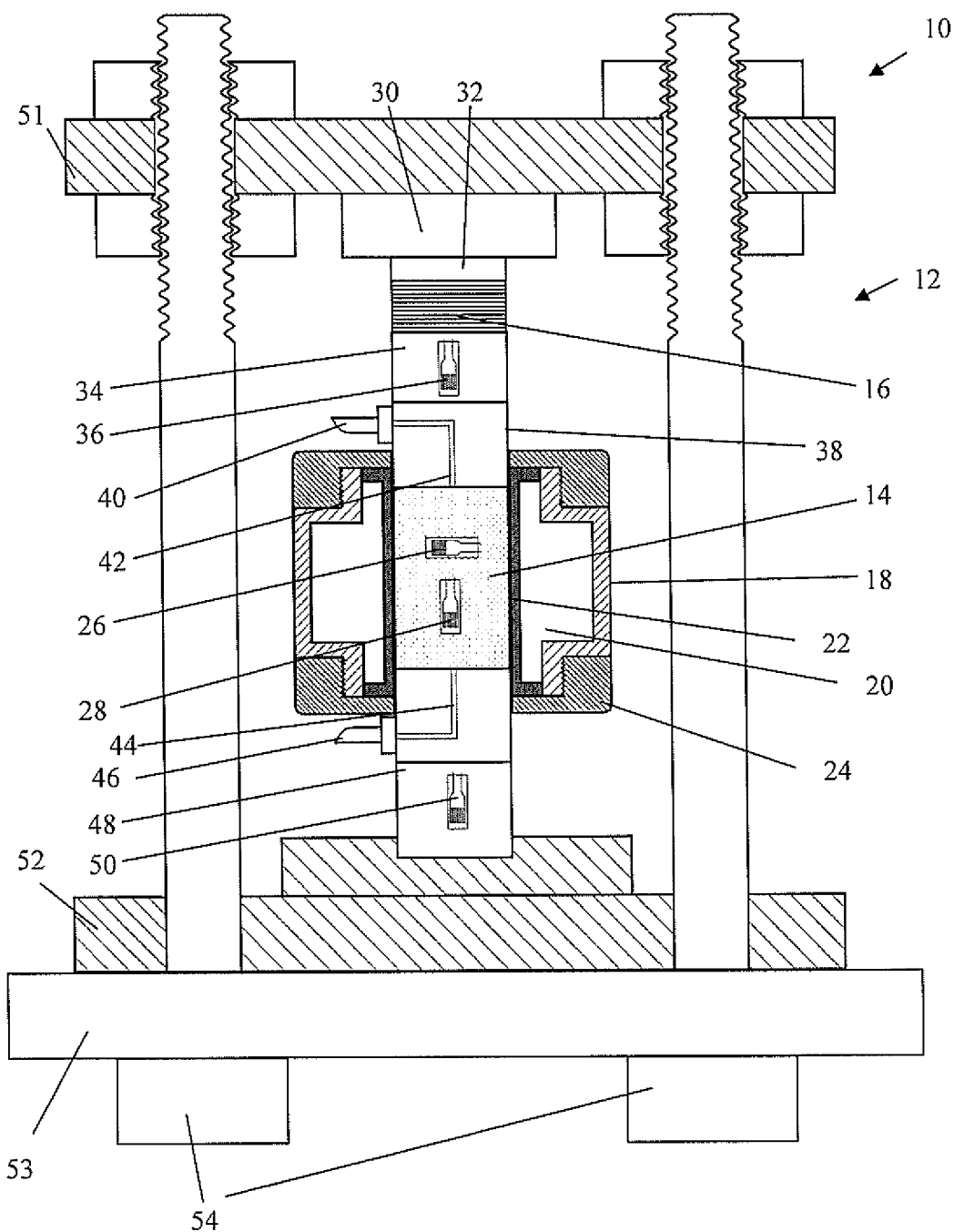
FIG. 1 is a schematic drawing showing an apparatus for characterising mechanical properties of a sample in accordance with an embodiment of the present invention.

FIG. 1 shows an apparatus 10 for characterising mechanical properties of a sample. Typically, the mechanical properties will be elastic or anelastic properties of the sample, wherein the sample is a core sample taken from a region of geological interest for example for exploration.

The apparatus 10 is arranged to subject the sample to conditions to which it would be typically subjected to in a subsurface location and to allow appropriate measurements of mechanical properties to be made under such conditions.

To achieve this, the apparatus 10 comprises a structure 12 for supporting a sample 14 and for applying a first pressure to the sample 14 in a first direction. In this example, the first pressure is applied by a hydraulic pressure machine 30 having a piston 32 that directs the force in an axial direction with respect to the sample 14. The hydraulic machine 30 is in fluidal communication with a pressure source (not shown), such as via an appropriate hydraulic fluid. Such a force may be used to represent typical axial pressures experienced by the sample 14 if it were in a subsurface region.

The apparatus 10 further comprises an actuator 16 for modulating the first pressure. In this example, the actuator 16 is a multilayer piezoelectric actuator and is arranged in line with the piston 32. To function under the pressure applied by the hydraulic pressure machine 30, the actuator 16 in this example has a high maximum load limit, such as a maximum load limit greater than 60,000N. Further, the actuator 16 has a high mechanical resonance, for example greater than 20 kHz so as to reduce its effect on the measurement frequency range which may be from 0 Hz to approximately 20 kHz.

In modulating the first pressure, the actuator 16 may be used to simulate an influence of pressure waves that the sample 14 would typically be subjected to in a subsurface location if sonic or seismic waves were directed towards the sample during geophysical surveys or similar.

As such, the actuator 16 is arranged to modulate the first pressure at a suitable frequency in the range of 0 Hz to 20 kHz. Further a ratio of a mean of the first pressure to the amount of modulation of the first pressure caused by the actuator 16 may be in the order of $10^3$ to $10^6$.

The apparatus also comprises a pressure applicator 18 for applying a second pressure to the sample 14 in a second direction that is transversal to the first direction. In this example, the pressure applicator 18 defines a passage 20 that radically surrounds the sample 14, the passage 20 being arranged between a sleeve 22 in which the sample 14 is located and a casing 24. The sleeve 22 may be formed from an elastomer material, however it will be appreciated that any appropriate resilient material may be used.

The passage 20 is filled with an appropriate hydraulic fluid, and be in fluidal communication with a pressure source (not shown) such that the hydraulic fluid in the passage 20 may exert a pressure (i.e. the second pressure) on the sample 14. In this example, the pressure that is exerted by the hydraulic fluid is in a radial direction towards the sample 14.

Further, the pressure source of the pressure applicator 18 is independent from the pressure source of the hydraulic machine 30 such that the first and second pressures may be controlled independently. For example the first pressure, which is in an axial direction with respect to the sample 14, could be set higher than the second pressure, which is in a radial direction with respect to the sample 14, so as to simulate an anisotropic stress field that the sample 14 may be subjected to in a typical subsurface location.

The apparatus 10 further comprises a radial strain gauge 26, arranged within or on the sample 14 so as to measure the radial strain component experienced by the sample 14, and an axial strain gauge 28, arranged within or on the sample 14 so as to measure the axial strain component experienced by the sample 14. Measurements obtained by strain gauges 26, 28 may be used in conjunction with measurements obtained by axial strain gauges 36 and 50 arranged to measure the axial strain experienced by aluminum calibration standard 34 and 48, which will experience the same first pressure as the sample 14. The aluminum standards 34 and 48 are arranged in such a way that the sample 14 is located between them.

The apparatus 10 further comprises a pore pressure control device 38 being arranged to allow fluids to flow through the sample 14, thereby providing means for controlling the pore pressure of the sample 14. In this example, the pore pressure control device 38, made from aluminum or any other material with low acoustic energy losses, comprises an inlet port 40 for receiving a fluid and an inlet passage 42 for introducing the fluid to the sample 14. Any introduced fluid may then flow through the sample 14 to an outlet passage 44, where it is directed to an outlet port 46. The inlet and outlet ports 40, 46 may be in fluid communication with any appropriate device or devices so as to allow the fluid to flow through the sample 14. For example, the inlet and outlet ports 40, 46 may be in fluid communication with a fluid reservoir and a recirculation device to allow for continuous flow of fluid through the sample 14.

The apparatus 10 is further arranged so as to reduce its resonance frequency. In one example, the apparatus 10 comprises first and second mass plates 53, 54 arranged at the top and bottom of the apparatus 10 respectively. The mass plates 53, 54 increase the overall mass of the apparatus 10 so as to reduce its resonance frequency, such as below 0.1 Hz. Further, due to their mass, the mass plates 53, 54 will reduce an amplitude of vibrations of the apparatus 10 at its resonance frequency.

The apparatus 10 may also be arranged on a damping platform 51 having damping devices 52 such as pneumatic pistons so as to isolate the apparatus 10 from environmental vibrations and to further dampen vibrations at the resonance frequency of the apparatus 10. Further, the hydraulic machine 30 also provides vibration damping.

Figure 2:
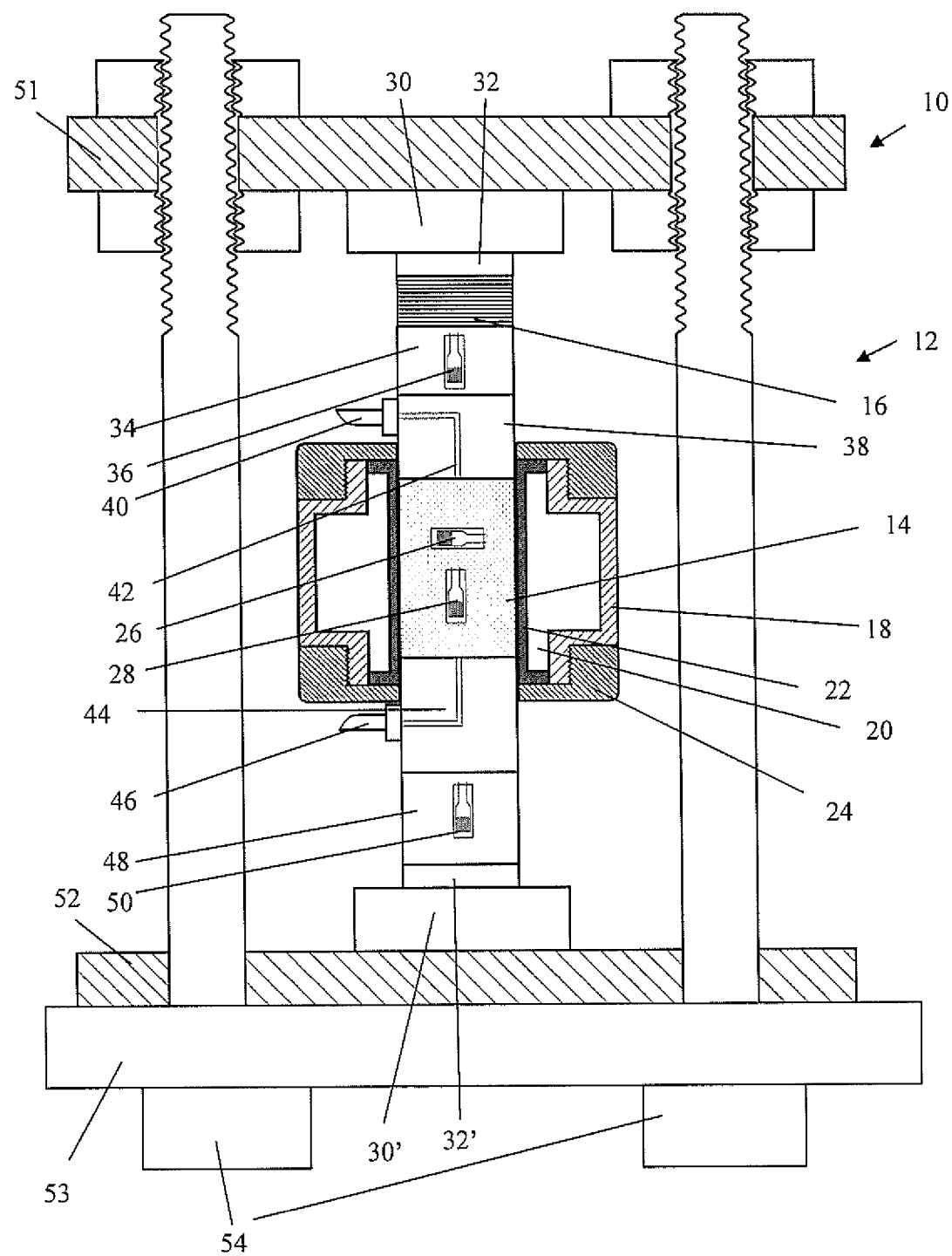
FIG. 2 is a schematic drawing showing an apparatus for characterising mechanical properties of a sample in accordance with a further embodiment of the present invention.
Figure 3:
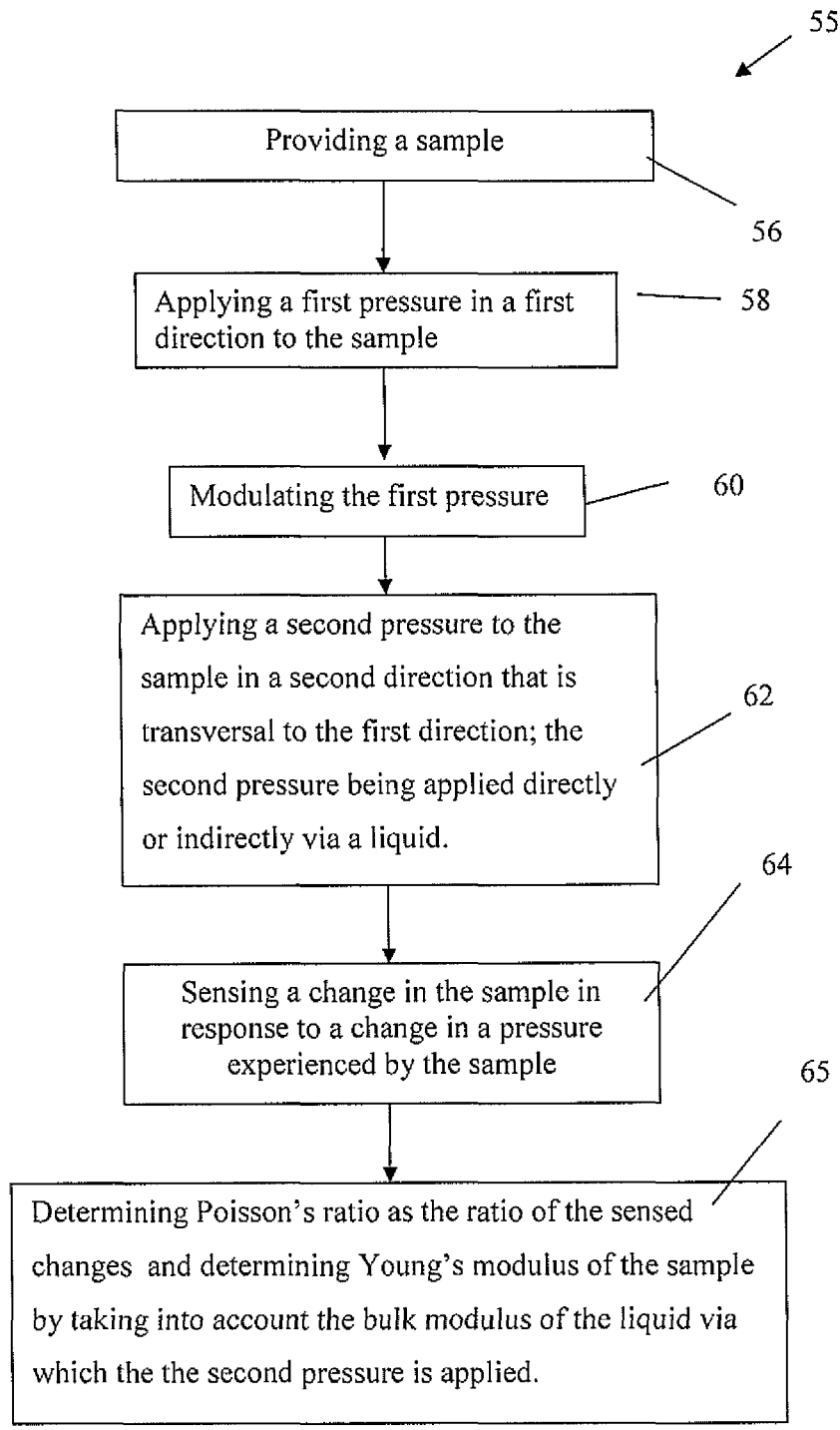
FIG. 3 is a flow diagram showing a method of characterizing mechanical properties of a sample in accordance with an embodiment of the present invention.

In an alternative embodiment, shown in FIG. 2, an apparatus 10' is provided with two opposing hydraulic machines 30, 30' each having respective pistons 32, 32' for applying the first pressure to the sample 14. Each hydraulic machine 30, 30' may be in fluidal communication with the same pressure source. Alternatively, each pressure machine 30, 30' may be in fluid communication with independent pressure sources so as to provide independent control of the pressure exerted by each pressure machine 30, 30' on the sample 14.

To further reduce vibrations experienced by the apparatus 10', each pressure machine 30, 30' may also provide vibration damping.

The apparatus 10, 10' may be used in a method 55 of characterising mechanical properties of the sample 14. In a first step 56, a sample 14 is provided. In this example, the sample 14 is a core sample and is held within the sleeve 22 of the apparatus 10, 10' such that the hydraulic machine 30 or machines 30, 30', the actuator 16, and the pressure applicator 18 may all exert pressures on the sample 14.

In a second step 58, a first pressure is applied in a first direction to the sample 14.

In this case, the first pressure is provided by the hydraulic machine 30 or machines 30, 30' and simulates the axial force that would be experience by the sample in a subsurface location.

In a third step 60, the first pressure is modulated by means of the actuator 16 at a frequency between 0 and 20 kHz so as to simulate sonic or seismic waves that the sample 14 would be subjected to during geophysical surveys or similar.

In a fourth step 62, a second pressure is applied to the sample 14 in a second direction that is transversal to the first direction by means of the pressure applicator 18. In this case, the pressure applicator 18 is exerting a force in a substantially radial direction towards the sample 14 so as to simulate radial forces that the sample 14 would experience in a subsurface location. In this example the sample is surrounded by sleeve 22 and the second pressure is applied via a hydraulic liquid that transmits the pressure to the sleeve 22, which in turn transmits the pressure to the sample 14. In an alternative embodiment the liquid may also be in direct contact with the sample (especially if the sample is non-porous).

In a fifth step 64, changes in the sample, such as the axial and radial strain experienced by the sample in response to the pressures exerted on it, are sensed. In this case, the changes are sensed by the radial and axial strain gauges 26, 28 and this information, in conjunction with reference strain information obtained by the axial strain gauge 36 associated with the aluminum calibration standard 34, may be used to characterise elastic or anelastic properties of the sample 14. This will be explained in more detail with reference to FIG. 4.

In a further step 65 the method 54 comprises determining Poisson's ratio as the ratio of the detected signals associated with the first and second pressures and determining Young's modulus of the sample by taking into account the bulk modulus of the liquid used for applying the second pressure.

Figure 4:
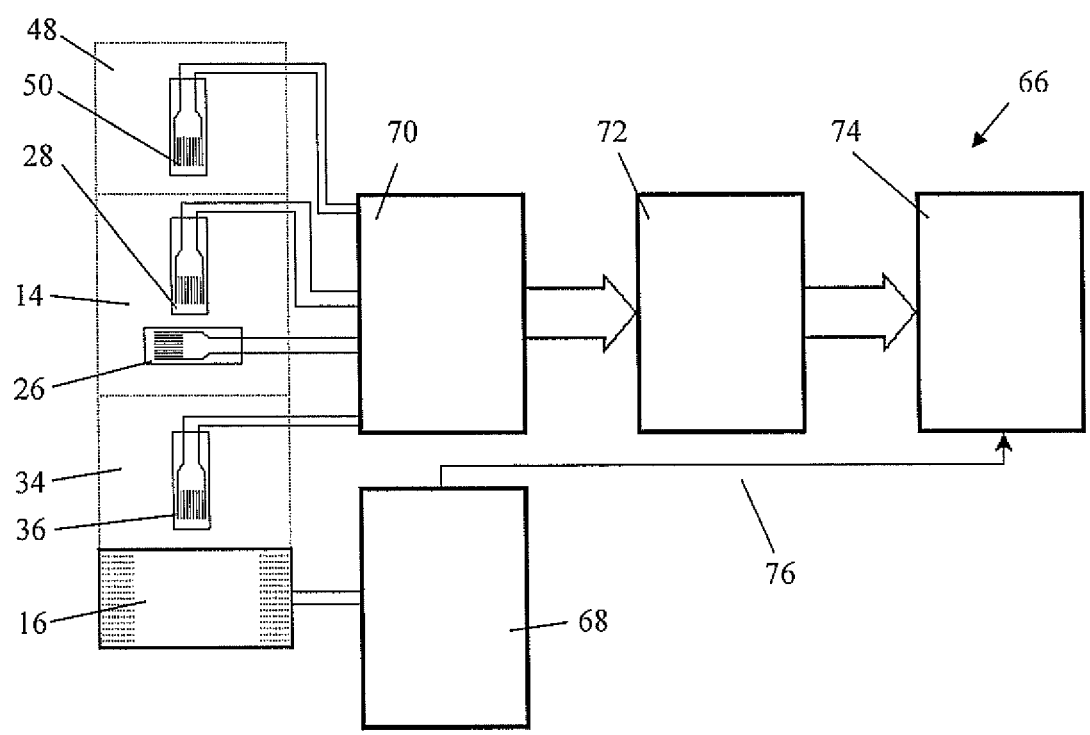
FIG. 4 is a schematic diagram showing electronic connections between elements of the apparatus of FIGS. 1 and 2.

FIG. 4 shows the actuator 16 arranged in line with the aluminum calibration standard 34, and its associated axial strain gauge 36, and the sample 14, and its associated radial and axial strain gauges 26, 28. The actuator 16, in this case a piezoelectric actuator, receives a periodic voltage signal from an oscillator 68 and transforms the voltage signal into mechanical stress, thereby causing displacements in the aluminum calibration standard 34 and the sample 14.

The displacements of the aluminum calibration standard 34 and the sample 14 modulate the conductivity of the strain gauges 26, 28, 36, which are transformed via a set of electrical bridges 70 into electrical signals. These signals are then communicated to an analogue to digital (AD) converter 72. The AD converter 72 digitises the signals and communicates the digitised signals to an acquisition computer 74 where the digitized signals are averaged and processed. The processing in acquisition computer 74 is synchronized with the oscillator 68 via a triggering signal 76.

As discussed, the radial and axial components of the strain experienced by the sample 14 are detected by the strain gauges 26, 28. The resulting digitised signals from these gauges 26, 28 are then used to calculate the Young's modulus and Poisson's ratio.

We assume that periodical stress is applied along a z-axis of Cartesian coordinate system with x and y, and z-axes, then from Hooke's law it follows that $$\varepsilon_{ij} = \frac{1}{E}(1+v)\sigma_{ij} - v\delta_{ij}\sigma_{\alpha\alpha}, (i = x, y, z; j = x, y, z) \quad (1)$$

where $\epsilon_{ij}$ are the elements of a rock strain tensor; $\sigma_{ij}$ are the elements of the stress tensor $$\sigma_{\alpha\alpha} = \sum_{i=x,y,z} \sigma_{ii};$$

Poisson's ratio $v$ can be found by $$v = \frac{c - \frac{\varepsilon_{xx}}{\varepsilon_{zz}}}{1 + c - 2c \cdot \frac{\varepsilon_{xx}}{\varepsilon_{zz}}}, \quad (2)$$

where $$c = \frac{\sigma_{xx}}{\sigma_{zz}}.$$

The Young's modulus of the rock E can be found from Eq. (1):

$$E = \sigma_{zz} \frac{(1+v)(1-2v)}{2v\varepsilon_{xx} + (1-v)\varepsilon_{zz}}, \quad (3)$$

The stress $\sigma_{zz}$ can be expressed through the parameters of the aluminum standard as $E_{al}\varepsilon_{zz}^{al}$, where $E_{al}$ is the known Young's modulus and $\varepsilon_{zz}^{al}$ is a measured amplitude of axial strain. consequently, the Young's modulus of the rock sample is $$E = E_{al} \frac{\varepsilon_{zz}^{al}(1+v)(1-2v)}{2v\varepsilon_{xx} + (1-v)\varepsilon_{zz}}. \quad (4)$$

It can be shown that the coefficient c, which is required for the determination of the Poisson's ratio $v$ in Eq. (2), is equal to $$c = k_l \frac{rL_s}{(R^2 - r^2)L \cdot E_{al}} \frac{\varepsilon_{xx}}{\varepsilon_{zz}^{al}}, \quad (5)$$

where $k_l$ is the bulk modulus of the hydraulic oil; $L_s$ and r are the length and radius of the sample; R is the internal radius of the core holder.

Using the Young's modulus determined by Eq. (4), we can find compressional and shear velocities:

$$V_p = \sqrt{\frac{E(1-v)}{(1+v)(1-2\sigma)\rho}}, \quad V_s = \sqrt{\frac{E}{2(1+v)\rho}}, \quad (6)$$

where $\rho$ is the density of the sample.

Such an anelastic parameter as extensional attenuation $Q_E^{-1}$ can be estimated as $\tan(\varphi)$, where $\varphi$ is the phase shift between the periodic stress, applied to a sample, and the strain caused by this stress in the sample:

$$Q_E^{-1} = \tan(\varphi). \quad (7)$$

The periodic stress $\sigma_{zz}$ produced by piezoelectric actuator 16 is directly applied to the aluminium calibration standard 34. Because the extensional attenuation in the aluminium standard 34 is negligible, the applied periodic stress and the strain in aluminium have the same phase. The aluminium standard 34 is, in turn, the source of the stress for the pore pressure control device 38 and the rock sample 14. Thus the extensional attenuation in the pore pressure control device 38 can also be neglected and the phase shift between the periodical strains in the rock sample 14 and the aluminium standard 34 is proportional to the extensional attenuation $Q_E^{-1}$ in the rock sample 14. The strain in the aluminium standard 48 has the same phase as the strain in the rock sample 14, and, therefore, the extensional attenuation $Q_E^{-1}$ can be measured as the phase shift co between periodic signals, which are detected by axial strain gauges 36 and 50 coupled with the aluminium standards 34 and 48 respectively.

The signals detected by strain gauges 36 and 50 are averaged and subjected to Fourier transformation. The resulting complex Fourier amplitudes $\dot{A}_{al}$ and $\dot{A}_s$, which are calculated at the frequency of the periodic voltage generated by the oscillator 68, are used to estimate the attenuation $Q_E^{-1}$:

$$Q_E^{-1} = \frac{\text{Im}(R)}{\text{Re}(R)} = \tan(\varphi) \approx \varphi, \quad (8)$$

where $$R = \frac{A_1}{A_2}$$

is the ratio of the complex amplitudes $A_1$ and $A_2$, corresponding to the signals obtained from the axial strain gauges 36 and 50 respectively.

With slightly less accuracy the attenuation $Q_E^{-1}$ can be also determined by expression $$Q_E^{-1} \approx \arctan\left(\frac{\text{Im}(A_1)}{\text{Re}(A_1)}\right) - \arctan\left(\frac{\text{Im}(A_2)}{\text{Re}(A_2)}\right) = \varphi. \quad (9)$$

Modifications and variations as would be apparent to a skilled addressee are determined to be within the scope of the present invention.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:
1. A method of characterizing elastic and anelastic properties of a sample, the method comprising the steps of:
   providing the sample;
   applying a first pressure in a first direction to the sample;
   modulating the first pressure periodically so that a ratio of a mean of the first pressure to the amount of modulation of the first pressure caused by the actuator is in the order of $10^3$ to $10^6$;
   applying a second pressure to the sample in a second direction that is transversal to the first direction; the second pressure being applied via a liquid that transfers the second pressure either directly or indirectly to the sample;
   sensing a first signal in response to a change in the first pressure experienced by the sample using a first sensor arranged within or on the sample;

sensing a second signal in response to a change in the second pressure experienced by the sample using a second sensor arranged within or on the sample;

detecting a third signal proportional to a strain and associated with the first pressure, the third signal being detected using a third sensor associated with a first calibration standard, wherein the third sensor and the associated first calibration standard are positioned at a location between the actuator modulating the first pressure and the sample;

detecting a fourth signal in response to a change in the first pressure, the fourth signal being detected using a fourth sensor associated with a second calibration standard, wherein the fourth sensor and the associated second calibration standard are positioned at a location such that the sample is located between that location and the actuator modulating the first pressure;

determining a phase shift between the periodic stress, applied to the sample, and the strain caused by this stress in the sample using the third signal;

determining a phase shift between the periodic stress, applied to the sample, and the strain caused by this stress in the sample using the fourth signal;

determining a phase shift between the periodic stress, applied to the sample, and the strain caused by this stress in the sample using the third or the fourth signal in conjunction with the first or the second signal;

determining an extensional attenuation in the sample using the determined phase shifts between the periodic stress, applied to the sample, and the strain caused by this stress in the sample; and characterizing the elastic and anelastic properties of the sample from the sensed signals and from the determined extensional attenuation.

\* \* \* \* \*